(12) United States Patent
Liao et al.

(10) Patent No.: US 9,884,859 B2
(45) Date of Patent: Feb. 6, 2018

(54) SOLID FORM OF PYRAZOLOPYRIDINE COMPOUND

(71) Applicant: SUNSHINE LAKE PHARMA CO., LTD., Dongguan, Guangdong (CN)

(72) Inventors: Shouzhu Liao, Dongguan (CN); Weijie Fan, Dongguan (CN); Zhongqing Wang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 0 days.

(21) Appl. No.: 15/027,432

(22) PCT Filed: Oct. 15, 2014

(86) PCT No.: PCT/CN2014/088680
§ 371 (c)(1),
(2) Date: Apr. 6, 2016

(87) PCT Pub. No.: WO2015/055124
PCT Pub. Date: Apr. 23, 2015

(65) Prior Publication Data
US 2016/0251349 A1 Sep. 1, 2016

(30) Foreign Application Priority Data
Oct. 17, 2013 (CN) .......................... 2013 1 0487493

(51) Int. Cl.
*C07D 471/04* (2006.01)
*A61K 31/506* (2006.01)

(52) U.S. Cl.
CPC .......... *C07D 471/04* (2013.01); *A61K 31/506* (2013.01)

(58) Field of Classification Search
USPC ............................ 514/255.05, 256, 269, 275
See application file for complete search history.

(56) References Cited

U.S. PATENT DOCUMENTS

| 7,173,037 B2 | 2/2007 | Alonso-Alija et al. |
| 8,492,544 B2 | 7/2013 | Mais et al. |
| 8,853,398 B2 * | 10/2014 | Mais .................... C07D 471/04 544/328 |
| 2011/0183999 A1 | 7/2011 | Grunenberg et al. |
| 2012/0316183 A1 | 12/2012 | Grunenberg et al. |

FOREIGN PATENT DOCUMENTS

| WO | WO2014/128109 | * | 8/2014 | .......... C07D 471/04 |
| WO | WO2014128109 A1 | | 8/2014 | |
| WO | WO2016113415 A1 | | 7/2016 | |

OTHER PUBLICATIONS

Connolly (http://epswww.unm.edu/media/pdf/06-Diffraction-II.pdf, 02/20012).*

* cited by examiner

*Primary Examiner* — Pancham Bakshi
(74) *Attorney, Agent, or Firm* — Kam W. Law; Squire Patton Boggs (US) LLP

(57) ABSTRACT

A novel crystalline form or amorphous of formula (I) and preparation method thereof are disclosed in present invention, wherein the novel crystalline form is substantially pure crystalline form I, form II, form III or form IV. The novel crystalline forms disclosed herein have good solubility, low hydroscopicity and good stability at high temperature (60° C.), high humidity (RH is 90%±5%) and/or under light (4500+/−500 Lux), which benefit for storage, meet the requirements of drug stability and therefore, making formula (I) suitable for formulation preparation and with high bioavailability.

(I)

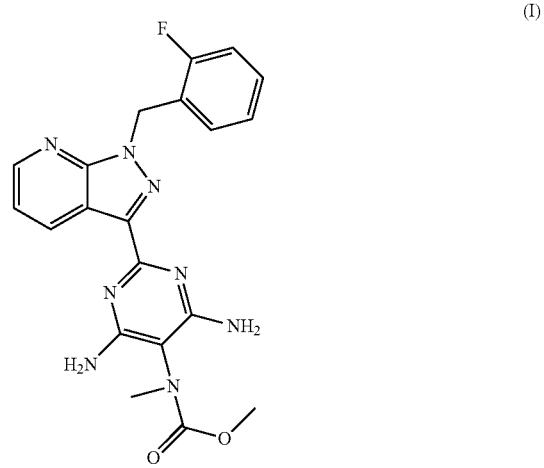

17 Claims, 9 Drawing Sheets

SOLID FORM OF PYRAZOLOPYRIDINE COMPOUND

CROSS-REFERENCE TO RELATED APPLICATIONS

This is a U.S. national stage application of the International Patent Application No. PCT/CN2014/088680, filed Oct. 15, 2014, which claims priorities to Chinese Patent Application No. 201310487493.1, filed Oct. 17, 2013, both of which are incorporated herein by reference in their entirety.

FIELD

The present disclosure relates to pharmaceutical field, particularly the present disclosure relates to novel crystalline forms or amorphous of pyrazolopyridine compounds, more particularly the present disclosure relates to a novel crystalline form or amorphous of methyl {4,6-diamino-2-[1-(2-fluorobenzyl)-1H-pyrazolo[3,4-B]pyridine-3-yl]pyrimidine-5-yl}N-methylcarbamate.

BACKGROUND

Riociguat, also known as methyl{4,6-diamino-2-[1-(2-fluorobenzyl)-1H-pyrazolo[3,4-B]pyridine-3-yl] pyrimidine-5-yl}N-methylcarbamate, has formula (I). Riociguat is the first of a new class of Guanylatecyclase (sGC) agonist, directly activates sGC and increases low levels of NO sensitivity, for treating pulmonary hypertension and chronic obstructive pulmonary hypertension.

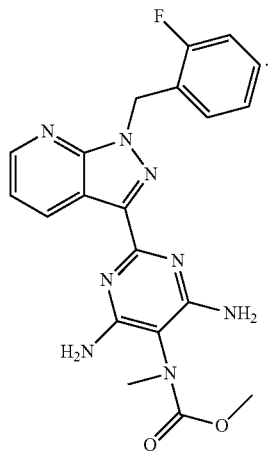

(I)

Many drugs may exist in different crystalline forms, which may have significant differences from each other inappearances, solubilities, melting points, dissolution rates, bioavailabilities, stability, efficacy and the like. So it is very important to think through the situation of different crystal forms in drug development.

The compound of formula (I) is first disclosed by U.S. Pat. No. 7,173,037, wherein example 8 discloses the preparation method of the compound of formula (I) wherein a crystal form of the compound of formula (I) is obtained by recrystallization from methanol. US 20110130410 disclosed a DMSO solvate of the compound of formula (I). However, we can't determine the crystal form of formula (I) for the above references do not fully characterize the polymorphs by XPRD, DSC, IR etc and their solubility, stability behavior in drug formulation.

Therefore, the crystalline behavior of formula (I), methyl{4,6-diamino-2-[1-(2-fluorobenzyl)-1H-pyrazolo[3,4-B]pyridine-3-yl] pyrimidine-5-yl}N-methylcarbamate, need to be well investigated to obtain the desired crystal form in order to fulfill the formulation requirements.

SUMMARY

In one aspect, provided herein is a novel crystalline form of the compound of formula (I)

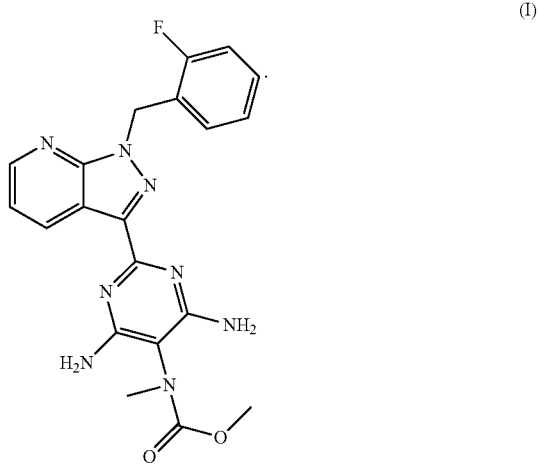 [SMILES: COC(=O)N(C)c1c(N)nc(-c2nn(Cc3ccccc3F)c3ncccc23)nc1N]

(I)

The crystalline form of a drug compound may have different chemical and physical properties, including melting point, chemical reactivity, apparent solubility, dissolution rate, optical and mechanical properties, vapor pressure and density. These properties may have a direct effect on the ability to process and/or manufacture the drug compound and the drug product, as well as on drug product stability, dissolution, and bioavailability. Thus the crystalline forms of the compound of formula (I) may affect the quality, safety, and efficacy of a drug product comprising the compound of formula (I).

According to embodiments of present disclosure, the inventors investigate whether the compound of formula (I) may present in a polymorph form. Unexpectedly, the inventors have found that the compound of formula (I) may present in many novel crystalline forms including form I, form II, form III and form IV.

In some embodiments, the crystalline form of the compound of formula (I) is crystalline form I. In some embodiments, form I has an X-ray powder diffraction (XRPD) pattern comprising one or more peaks at about 25.47, 17.69 and 27.23 degrees in term of two theta. In some embodiments, form I has an XRPD comprising one or more peaks at about 25.47, 17.69, 27.23, 8.99, 6.68, 14.24, 20.27 and 19.67 degrees in term of two theta. In some embodiments, form I has an XRPD comprising one or more peaks at about 25.47, 17.69, 27.23, 8.99, 6.68, 14.24, 20.27, 19.67, 20.95, 30.76 and 20.57 degrees in term of two theta. In some embodiments, form I has an XRPD substantially as depicted in FIG. 1, wherein the peak at about 25.47 degree in term of two theta has a relative intensity of at least about 50%, at least about 60%, at least about 70%, at least about 80%, at least about 90% or at about 100% with respect to the strongest peak in the XRPD.

In some embodiments, the characteristics of form I may be detected, identified, classified and characterized using well-known techniques, such as in certain embodiments, the form I has a DSC curve comprising the endothermic peak at about 268.95° C. In certain embodiments, form I has a DSC curve substantially as depicted in FIG. 2.

In some embodiments, the crystalline form of the compound of formula (I) is crystalline form II. In some embodiments, form II has an X-ray powder diffraction (XRPD) pattern comprising one or more peaks at about 25.40, 13.86, 17.21 and 22.71 degrees in term of two theta. In certain embodiments, form II has an XRPD comprising one or more peaks at about 25.40, 13.86, 17.21, 22.71, 11.13, 12.56, 24.89 and 22.47 degrees in term of two theta. In certain embodiments, form II has an XRPD comprising one or more peaks at about 25.40, 13.86, 17.21, 22.71, 11.13, 12.56, 24.89, 22.47, 26.04 and 29.92 degrees in term of two theta. In some embodiments, form II has an XRPD substantially as depicted in FIG. 3 wherein the peak at about 25.40 degree in term of two theta has a relative intensity of at least about 50%, at least about 60%, at least about 70%, at least about 80%, at least about 90% or at about 100% with respect to the strongest peak in the XRPD.

In some embodiments, the characteristics of form II may be detected, identified, classified and characterized using well-known techniques, such as in certain embodiments, the form II has a DSC curve comprising the endothermic peak at about 268.45° C. In certain embodiments, form II has a DSC curve substantially as depicted in FIG. 4.

In some embodiments, the crystalline form of the compound of formula (I) is crystalline form III. In some embodiments, form III has an X-ray powder diffraction (XRPD) pattern comprising one or more peaks at about 25.44, 13.88, 17.23, 15.14 degrees in term of two theta. In certain embodiments, form III has an XRPD comprising one or more peaks at about 25.44, 13.88, 17.23, 15.14, 22.75, 12.60, 11.17, 9.02, 17.66, 22.52, 24.94, 17.53 and 6.68 degrees in term of two theta. In some embodiments, form III has an XRPD substantially as depicted in FIG. 5 and the peak at about 25.44 degree in term of two theta has a relative intensity of at least about 50%, at least about 60%, at least about 70%, at least about 80%, at least about 90% or at about 100% with respect to the strongest peak in the XRPD.

In some embodiments, the characteristics of form III may be detected, identified, classified and characterized using well-known techniques, such as in certain embodiments, the form III has a DSC curve comprising the endothermic peak at about 267.80° C. In certain embodiments, form III has a DSC curve substantially as depicted in FIG. 6.

In some embodiments, the crystalline form of the compound of formula (I) is crystalline form IV. In some embodiments, form IV has an X-ray powder diffraction (XRPD) pattern comprising one or more peaks at about 20.01, 27.03, 8.21 degrees in term of two theta. In certain embodiments, form IV has an XRPD comprising one or more peaks at about 20.01, 27.03, 8.21, 18.15 and 27.38 degrees in term of two theta. In certain embodiments, form IV has an XRPD comprising one or more peaks at about 20.01, 27.03, 8.21, 18.15, 27.38, 19.22, 26.34, 29.38, 8.57, 14.45 and 7.15 degrees in term of two theta. In some embodiments, form IV has an XRPD substantially as depicted in FIG. 7 wherein the peak at about 20.01 degree in term of two theta has a relative intensity of at least about 50%, at least about 60%, at least about 70%, at least about 80%, at least about 90% or at about 100% with respect to the strongest peak in the XRPD.

In some embodiments, the characteristics of form (IV) can be detected, identified, classified and characterized using well-known techniques, such as in certain embodiments, the form IV has an DSC curve comprising the endothermic peak at about 266.88° C. In certain embodiments, form IV has a DSC curve substantially as depicted in FIG. 8.

The present disclosure contemplates that any one of the solid forms of the compound of formula (I) as described herein can exist in the presence of the any other of the solid forms or mixtures thereof. Accordingly, in one embodiment, the present invention provides the crystalline form, the liquid crystalline form or the amorphous form of the compound of formula (I) as described herein, wherein the crystalline, liquid crystalline or amorphous form is present in a solid form that includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of formula (I). For example, in one embodiment is a solid form of the compound of formula (I) comprising a crystalline form of the compound of formula (I) that has any one of the powder X-ray diffraction patterns, Raman spectra, IR spectra and/or NMR spectra described above, wherein said solid form includes less than 95%, less than 90%, less than 80%, less than 70%, less than 60%, less than 50%, less than 40%, less than 30%, less than 20%, less than 10%, less than 5%, less than 3%, or less than 1% by weight of any other physical forms of the compound of formula (I).

Provided herein is a novel crystalline form of the compound of formula (I) comprising form I, form II, form III or form IV. The crystalline forms disclosed herein may have good solubility, low hydroscopicity and may be stable under high temperature (60° C.), high related humidity (RH is 90%±5%) and/or under light (4500+/−500 Lux), which benefit for storage, meet the requirements of drug stability and therefore make the compound of formula (I) suitable for formulation preparation and with high bioavailability.

Also disclosed herein is a method for preparing the crystalline forms I to form IV of the compound of formula (I), and the process comprises dissolving any solid forms of the compound of formula (I) in a good solvent to form a solution, forming crystals by reducing the temperature of the solution or removing proportion of the solvent or adding anti-solvent to the solution, and collect the crystal.

In some embodiments, the solid form of the compound is amorphous form or DMSO solvate disclosed by U.S. patent application No. 20110130410. In some embodiments, the compound of formula (I) is prepared according to the process disclosed in Chinese patent application 03816160.5.

In some embodiments, dissolving the compound of formula (I) with a good solvent may be promoted by a method known to the person skilled in the art, such as stirring, heating to reflux, sonication or shaking or any combination thereof. In some embodiments, the compound of formula (I) is dissolved by stirring and heating the reaction mixture to reflux.

In some embodiments, the temperature of the solution is reduced to from about −10° C. to about 40° C. The temperature for crystallization is from about −10° C. to about 40° C. In certain embodiments, the crystal is formed at room temperature.

In some embodiments, the way to remove proportion of the solvent comprises distillation (atmospheric or vacuum distillation) or evaporation or any combination thereof, and the amount of the removed solvent is from about 20% to about 90% with respect to the total volume of the solution. In certain embodiments, the amount of removed solvent is about 30% with respect to the total volume of the solution.

In some embodiments, the crystalline forms of the compound of formula (I) disclosed herein may be prepared by dissolving the compound of formula (I) in a good solvent at room temperature to form a solution, and forming crystals by adding the solution to an anti-solvent or adding an anti-solvent to the solution.

The solubility of the compound of formula (I) in the anti-solvent is less than in the good solvent with a solubility difference being about 10%, about 20%, about 30%, about 40%, about 50%, about 60%, about 70% or about 80% based on the solubility in the good solvent. Therefore, the term "anti-solvent" described herein is relative to a "good solvent", and the anti-solvent may be a polar or a non-polar solvent In some embodiments, a sufficient amount of a seed is added to promote a particular crystalline form of the compound of formula (I) such as crystalline forms I, form II, form III, or form IV. The seed refers to a small single crystal from which a larger crystal of the same or different crystalline form may be grown in certain embodiments, the small single crystal and the larger crystal are of a same solid form. In some embodiments, the small single crystal and the larger crystal are of the different solid forms.

The crystals may be isolated and/or purified by vacuum filtration, gravity filtration, suction filtration or a combination thereof. The isolated crystals may carry with some mother liquor. Therefore, the isolated crystals may be further washed with suitable solvent and then dried. In certain embodiments, the isolated crystals are washed with the crystallization solvent or water.

The good solvent or the anti-solvent may be one or more polar solvents, one or more non-polar solvents or any combination thereof, wherein the good solvent or the anti-solvent is selected from dimethyl formamide (DMF), dimethyl sulfoxide (DMSO), N-methyl-2-pyrrolidone (NMP) water, alcohol solvents, ether solvents, ketone solvents, ester solvents, aromatic hydrocarbon solvents, alkane solvents, nitrile solvents and any combination thereof, wherein the alcohol solvents are selected from methanol, ethanol, n-propanol, iso-propanol, ethylene glycol, 1,3-propanediol, 1,2-propylene glycol, 1,1,1-trichloro-2-methylpropan-2-ol and any combination thereof, wherein the ether solvents are selected from tetrahydrofuran (THF), methyl tert-butyl ether (MTBE), 1,4-dioxane and any combination thereof, and the ketone solvents may be selected from acetone, methyl ethyl ketone, 4-methyl-2-pentanone and any combination thereof, and the ester solvents may be selected from ethyl acetate, iso-propyl acetate, n-butyl acetate, tert-butyl acetate and any combination thereof, and the alkane solvents may be selected from dichloromethane, chloroform, hexane, cyclohexane, pentane heptane and any combination thereof, and the aromatic hydrocarbon solvents may be selected from benzene, toluene and any combination thereof, and the nitrile solvents may be selected from acetonitrile, malononitrile and any combination thereof.

In some embodiments, the good solvent or anti-solvent is selected from one or more of NMP, DMF, ethyl acetate, water, methanol, ethanol, ethylene glycol, isopropanol, n-propanol, n-butanol, tert-butanol, THF, methylene chloride, DMSO, ethyl acetate, acetone, acetonitrile, 1,4-dioxane.

In some embodiments, the good solvent or anti-solvent is selected from one or more of dichloromethane, methanol, ethanol, acetone, THF, NMP, DMF, DCM, 1, 4-dioxane, ethylene glycol, ethylene DMF, ethylene NMP, DMSO, EtOH, isopropanol, n-butanol, tert-butanol, n-propanol, acetonitrile, isopropyl acetate and n-butanone.

In some embodiments, the crystalline form I of the compound of formula (I) is formed from the good solvent, wherein the good solvent is selected from one or more of methanol, ethanol, acetone, THF, ethylene glycol, 1,4-dioxane, methylene chloride.

In some other embodiments, the crystalline form I of the compound of formula (I) can be formed, wherein the good solvent is selected from DMF, NMP or DMSO while the anti-solvent is selected from $H_2O$, ethyl acetate or ethanol.

In some embodiments, the crystalline form II of the compound of formula (I) can be formed, wherein the good solvent is selected from one or more of ethanol, isopropanol, n-butanol, ethylene glycol or tert-butanol.

In some other embodiments, the crystalline form II of the compound of formula (I) can be formed, wherein the good solvent is DMSO while the anti-solvent is $H_2O$.

In some embodiments, provided herein is a process for preparing the crystalline form I of the compound of formula (I), comprising a solution of the compound of formula (I) in DMSO with a temperature of 70° C. to 90° C. was added slowly to water with a temperature of 70° C. to 90° C., after the solution was added completely, the temperature was reduced to 25° C. below, and stirred for 1 hour to 24 hour.

In some embodiments, the crystalline form III of the compound of formula (I) can be formed, and the good solvent is selected from one or more of n-propanol, 1, 4-dioxane, acetonitrile or isopropyl acetate.

In some other embodiments, the crystalline form III of the compound of formula (I) can be formed, and the good solvent is NMP, DMSO or DMF while the anti-solvent is $H_2O$ ethanol and any combination thereof.

In some embodiments, the crystalline form IV of the compound of formula (I) can be formed, and the good solvent is butanone.

In some embodiments, the crystalline form I of the compound of formula (I) can be formed comprising adding the compound of formula (I) to ethanol, heating the mixture to a temperature from about 50° C. to a refluxing temperature of the solvent system to form a solution, cooling the solution and removing proportion of the solvent to form the crystals, stirring the result solution at room temperature for about 0.5 h to 36 h and collecting the crystals.

In some embodiments, the crystalline form II of the compound of formula (I) may be formed comprising adding the compound of formula (I) to ethanol, heating the mixture to a temperature from about 50° C. to the refluxing temperature of the solvent to form a solution, slowly cooling the solution to room temperature and sealing the solution, then stirring the result solution for about 1 h to 300 h and collecting the crystals.

In some embodiments, the crystalline form I of the compound of formula (I) can be formed comprising mixing the compound of formula (I) with 1, 4-dioxane, heating the mixture to a temperature at about 101° C. to form a solution, after cooling down to room temperature and stirring openly to allow evaporate naturally for a while, then sealing and stirring the result solution for about 1 h to 300 h and collecting the crystals.

In some embodiments, crystalline form III of the compound of formula (I) can be formed comprising mixing the compound of formula (I) with 1, 4-dioxane, heating and stirring the mixture to reflux until the solid is completely dissolved to form a solution, then slowly cooling the solution to room temperature and sealing the solution, stirring the solution for about 1 h to 300 h and collecting the crystals.

In some embodiments, crystalline form I of the compound of formula (I) can be formed comprising adding the mixture of the compound of formula (I) and ethylene glycol to reaction flask, heating and stirring the mixture to about 140° C. until the solid is completely dissolved to form a solution, after cooling the solution to room temperature and openly stirring to allow evaporate naturally for a while, then sealing the solution, stirring the solution for about 1 h to 300 h and collecting the crystals.

The crystalline form II of the compound of formula (I) can be formed comprising adding the mixture of the compound of formula (I) and ethylene glycol to reaction flask, heating and stirring the mixture to about 140° C. until the solid is completely dissolved to form a solution, then slowly cooling the solution to room temperature and sealing the solution, stirring for about 1 h to 300 h and collecting the crystals.

According to the process of the crystal form of the compound of formula (I) herein, substantially pure crystalline form I, form II, form III and form IV of the compound of formula (I) can be prepared through transforming any forms of formula (I) to the another expected crystal form of the compound of formula (I).

The process of the crystal form of the compound of formula (I) herein is simple, moderate, accorded with GMP requirement and suitable for industrialization The amorphous of the compound of formula (I) disclosed herein is substantially pure, wherein the X-ray powder diffraction pattern is depict as in FIG. 9. In some embodiments, the amorphous of the compound of formula (I) is prepared by spray drying.

As used herein, the term "spray drying" generally refers to the process comprising dispersing the liquid into tiny droplets (atomization) and quickly removing solvent from the mixture thereof.

The drug formulations comprising the novel crystalline form or amorphous of the compound of formula (I) disclosed herein may be used in treating cardiovascular disease, hypertension, thromboembolic disease, ischemia and sexual dysfunction in a patient.

The novel crystalline form or amorphous of the compound of formula (I) disclosed herein can be used in treating cardiovascular disease, hypertension, thromboembolic disease, ischemia and sexual dysfunction in a patient.

Also provides herein is the use of the crystalline form or amorphous of the compound of formula (I) in the drug used to treating cardiovascular disease, hypertension, thromboembolic disease, ischemia and sexual dysfunction in a patient.

Also provided herein is a pharmaceutical composition comprising a therapeutically effective amount of a crystalline form of the compound of formula (I), wherein the crystalline form is form I, form II, form III, form IV and one or more pharmaceutically acceptable carriers or excipients.

Also provided herein is a pharmaceutical composition comprises a pharmaceutically acceptable carrier and a therapeutically effective amount of amorphous of the compound of formula (I).

The pharmaceutical composition as disclosed herein can be administrated through being compacted into a dosage form, such as tablets, capsules (wherein every one of the capsules comprising formulations of sustained release or timed release), pills, powders, tinctures, deflocculants, syrupands or emulsifiers. Also can be administrated in intravenous (infusion solutions), intraperitoneal, subcutaneous, intramuscular forms.

The dosage forms used herein may be known by one skilled in the art. The dosage form may be administrated singly, and usually may be administrated together with a pharmaceutical carrier selected according to the way of administration and the standard pharmacy practice. Generally achieved by using appropriate non-toxic inert medicinal excipient comprising carriers (such as microcrystalline cellulose), solvents (such as polyethyleneglycol), emulsifiers (such as sodium lauryl sulfate), dispersants (such as polyvinylpyrrolidone), Synthetic and natural biopolymers (such as albumin), stabilizer (such as antioxidant of ascorbic acid), colorants (such as inorganic pigments of iron oxides) or corrective agents and/or taste-masking agents. In some appropriate cases, the active ingredients of the compound of formula (I) may exist in one or more carriers disclosed herein in the form of microencapsulation.

The pharmaceutically effective amount of the compound of formula (I) is from about 0.1% to about 99.5% base on the total weight of the pharmaceutical composition, and in some embodiments, the mass fraction of the compound of formula (I) can be from about 0.5% to about 95% in the pharmaceutical preparations thereof.

In some embodiments, some other active ingredients may also be included in the above mentioned pharmaceutical preparations in addition to the crystalline form of the compound of formula (I) in present invention.

BRIEF DESCRIPTION OF THE DRAWINGS

These and other aspects and advantages of embodiments of the present disclosure will become apparent and more readily appreciated from the following descriptions made with reference to the accompanying drawings, in which.

DETAILED DESCRIPTION

Figure 1:
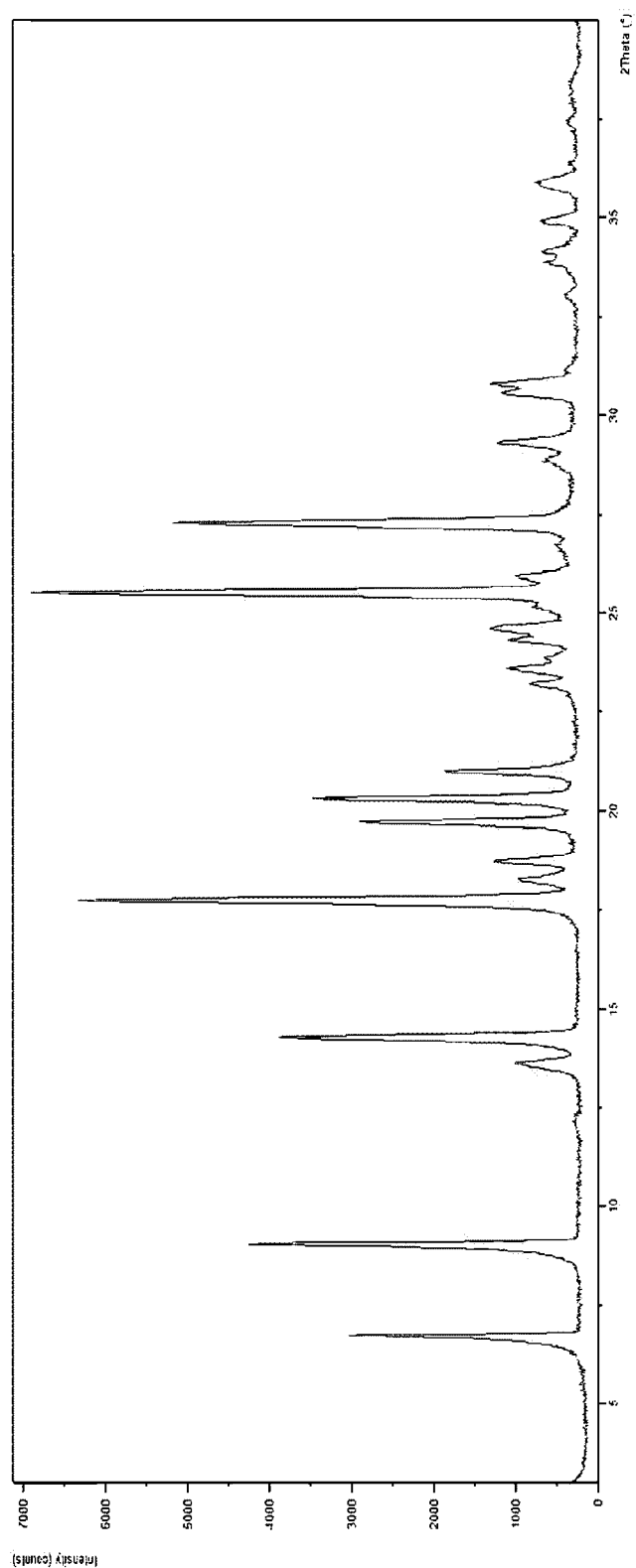
FIG. 1 depicts the X-ray powder diffractogram of the crystalline form I of the compound of formula (I) according to one example of present disclosure.
Figure 2:
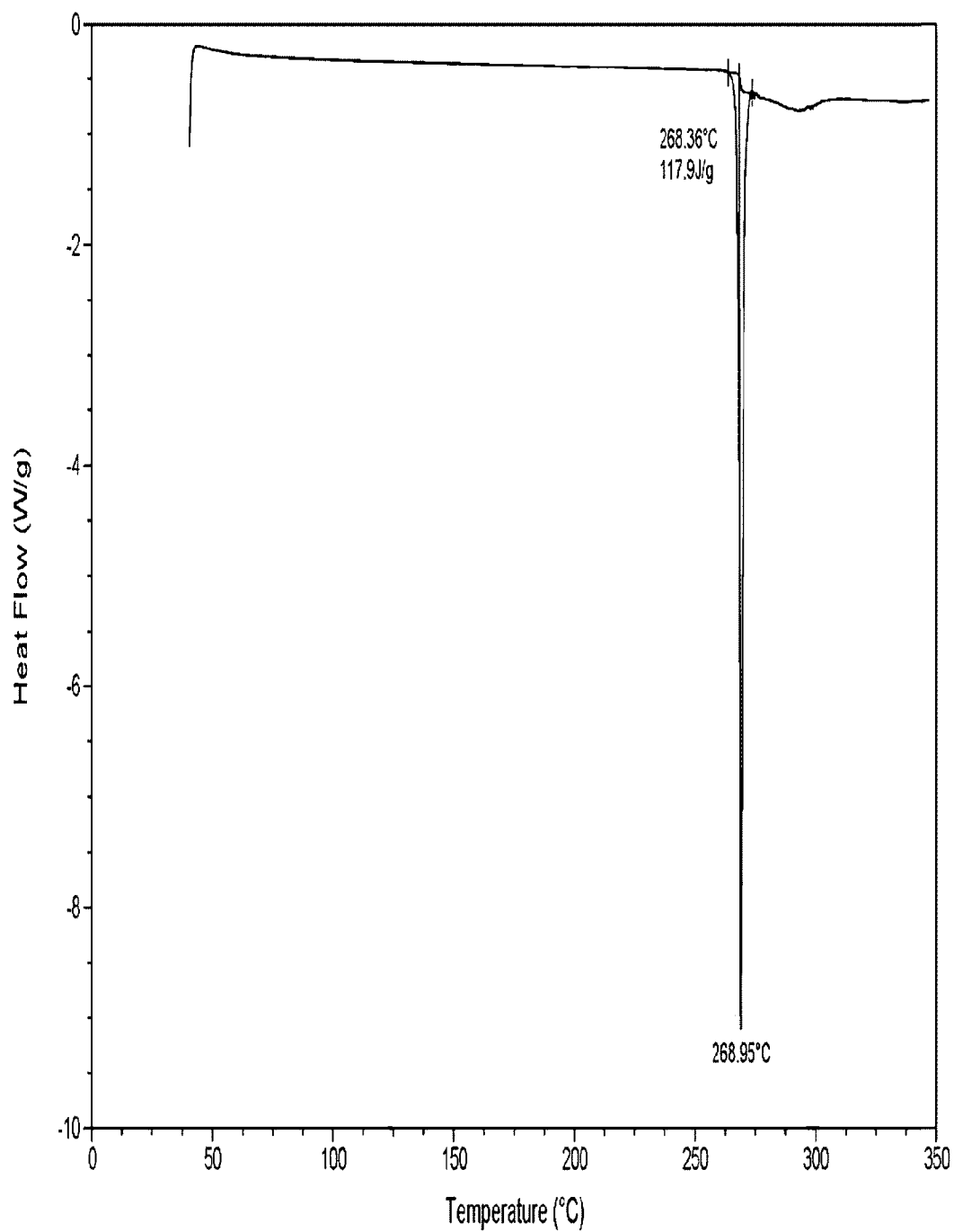
FIG. 2 depicts the differential scanning calorimeter (DSC) curve of the crystalline form I of the compound of formula (I) according to one example of present disclosure.

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols, and reagents which are reported in the publications and which might be used in connection with the invention. Nothing herein is to be construed as an admission that the invention is not entitled to antedate such disclosure by virtue of prior invention.

Definition

Otherwise stated, the following definitions may be use throughout the disclosure.

As used herein, the term "the compound of formula (I)" refers to the compound with chemical name of methyl{4,6-diamino-2-[1-(2-fluorobenzyl)-1H-pyrazolo[3,4-B] pyridine-3-yl] pyrimidine-5-yl}N-methylcarbamate.

As used herein, the term "crystal form" refers to the existing state of solid compounds especially the various parameters collection of the ions, atoms or molecular composition, the symmetric properties and the unique ordered arrangement of molecules in the crystal lattice of the compound.

As used herein, the term "amorphous" refers to the order less arrangement of particles (ions, atoms or molecules) of the compound in three-dimensional space.

As used herein, an X-ray powder diffraction pattern that is "substantially as depicted" in a figure refers to an X-ray powder diffraction pattern having at least 50%, at least 60%, at least 70%, at least 80%, at least 90%, at least 95%, or at least 99% of the peaks shown in the figure.

As used herein, the term "relative intensity" refers to the intensity of a peak with respect to the intensity of the strongest peak in the X-ray powder diffraction (XRPD) pattern which is regarded as 100%.

As used herein, the term "good solvent" refers to a solvent in which the compound of formula (I) has a solubility greater than 1 g/L, greater than 2 g/L, greater than 3 g/L, greater than 4 g/L, greater than 5 g/L, greater than 6 g/L, greater than 7 g/L, greater than 8 g/L, greater than 9 g/L, greater than 10 g/L, greater than 15 g/L, greater than 20 g/L, greater than 30 g/L, greater than 40 g/L, greater than 50 g/L, greater than 60 g/L, greater than 70 g/L, greater than 80 g/L, or greater than 100 g/L of the solvent. In some embodiments, the solubility of the compound of formula (I) in the good solvent is greater than the solubility of the compound of formula (I) in the anti-solvent. In certain embodiments, the solubility difference between the good solvent and anti-solvent is about 10%, 20%, 30%, 40%, 50%, 60%, 70%, 80% or 90%, based on the solubility of the good solvent. In some embodiments, the solubility of the good solvent is about 10%, 20%, 30%, 40%, 50%, 60%, 70%, 80% or 90% higher than anti-solvent.

As used herein, the term "anti-solvent" refers to a solvent which can promote super saturation and/or crystallization. In some embodiments, the solubility of the compound of formula (I) in the anti-solvent is less than 0.001 g/L, less than 0.01 g/L, less than 0.1 g/L, less than 0.2 g/L, less than 0.3 g/L, less than 0.4 g/L, less than 0.5 g/L, less than 0.6 g/L, less than 0.8 g/L, less than 1 g/L, less than 2 g/L, less than 3 g/L, less than 4 g/L, less than 5 g/L, less than 6 g/L, less than 7 g/L, less than 8 g/L, less than 9 g/L, or less than 10 g/L of the anti-solvent.

As used herein, the term "room temperature" refers to a temperature from about 18° C. to about 35° C. or a temperature from about 20° C. to about 24° C. or a temperature at about 22° C.

As used herein, the term "overnight" refers to a period of from about 6 hours to about 24 hours, or from about 8 hours to about 12 hours.

As used herein, when referring to a spectrum and/or to data presented in a graph, the term "peak" refers to a feature that one skilled in the art would recognize as not attributable to background noise.

In the following description, all numbers disclosed herein are approximate values, regardless whether the word "about" or "approximate" is used in connection therewith. The value of each number may differ by 1%, 2%, 5%, 7%, 8%, 10%, 15% or 20%.

In the context, degree (°) is the basic unit of the data of two theta in the X-ray powder diffraction pattern.

The 2theta (2θ) and/or the diffraction peak value at the X-ray powder diffraction (XRPD) pattern may show measurement error due to the measurement instruments or measurement samples and the like. To be specific, the measurement error may be within the range of about ±0.3, or about ±0.2 or about ±0.1 unit, for example, in the following description, "an X-ray powder diffraction pattern comprises one peak at about 25.44" it means an X-ray powder diffraction pattern comprises one peak at 25.44±0.2.

The position and value of the endothermic peak at the differential scanning calorimeter (DSC) pattern may show measurement error due to the measurement instruments or measurement samples and the like. The measurement error may be 5° C. or less, 4° C. or less, 3° C. or less, 2° C. or less. Therefore, the position and value of the endothermic peak can't be regard as absolutely.

EXAMPLES

The embodiments of the present disclosure is a novel crystalline form and amorphous of the compound of formula (I). Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way is obvious to the skilled in this art and is deemed to include in the present invention. Numeric ranges are inclusive of the numbers defining the range. Furthermore, numeric ranges are provided so that the range of values is recited in addition to the individual values within the recited range being specifically recited in the absence of the range.

Example 1

Preparation of Amorphous of the Compound of Formula (I)

Figure 9:
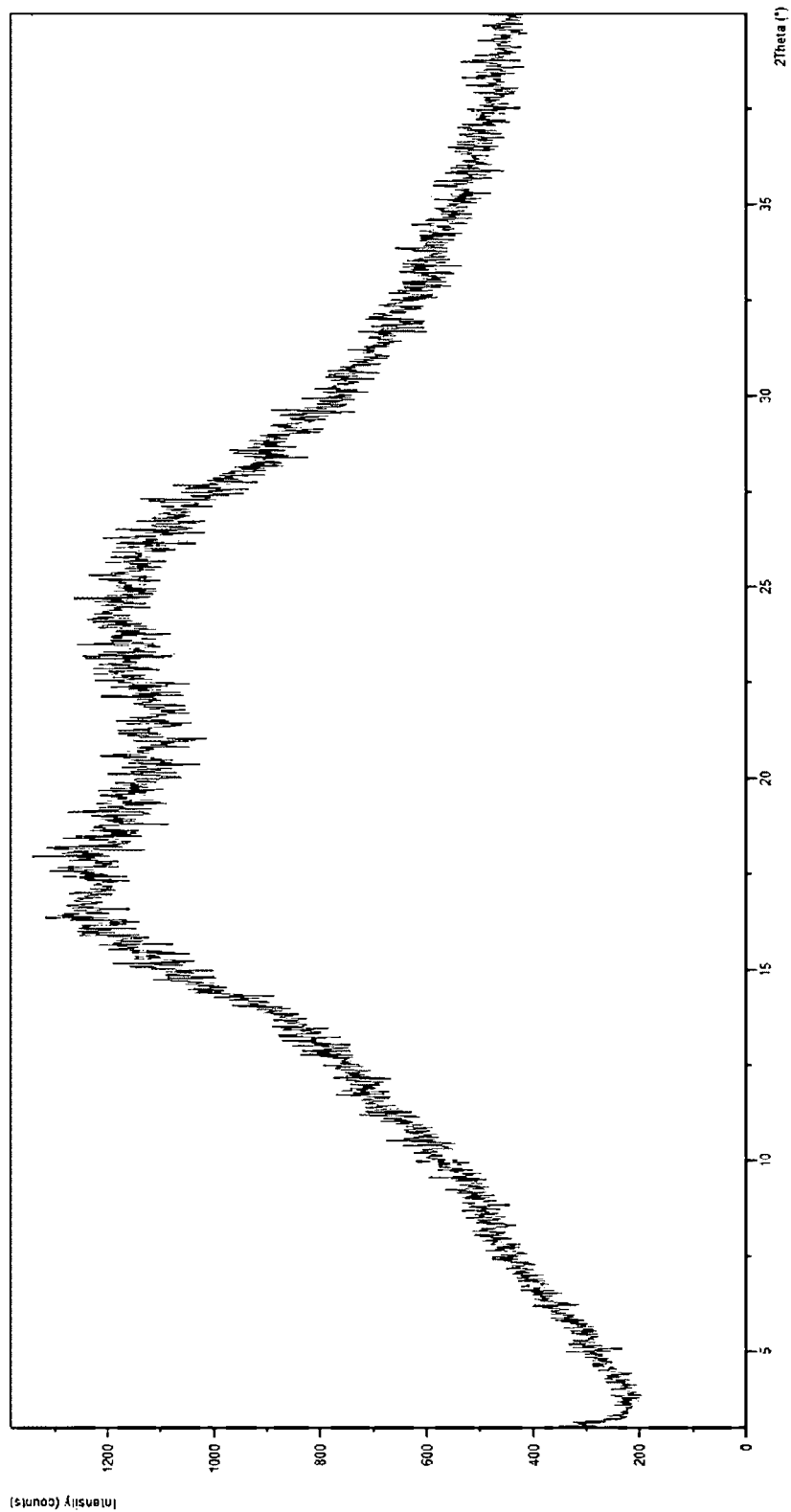
FIG. 9 depicts the X-ray powder diffractogram of the amorphous of the compound of formula (I) according to one example of present disclosure.

The compound of formula (I) (2 g) and dichloromethane (500 mL) were added to a reaction flask, heated to reflux and stirred until the solid was completely dissolved to form a clear solution. The solution was then transferred to BUCHI Mini Spray Dryer (B-290) spray drier and dried in the following detecting conditions: the inlet temperature was about 100° C., the outlet temperature was about 60° C., lashing velocity was 100% and the bump speed ability was 30% to form granules. The granules were collected and detected by PANalytical Empyreandiffractometer to give an X-ray powder diffractogram of the granules as depict in FIG. 9.

As used herein, the term "inlet temperature" is the temperature of the solution when coming into the spray drier and the term "outlet temperature" is the temperature of the gas when coming out of the spray drier.

The inlet and the outlet temperature can be modified if necessary according to the equipment, gas or some other experimental parameters. For example, as is known that the outlet temperature can be determined by parameters such as aspirator speed, air humidity, inlet temperature, spray air flow, rate of feed or concentration. Therefore, the outlet temperature would be determined by one skilled in this art through modifying the parameters.

Example 2-Example 15

Preparation of Crystalline Form I of the Compound of Formula (I)

Example 2

The compound of formula (I) (0.2 g) (prepared by example 1) and methanol (21 mL) were added to a reaction flask, heated to reflux and stirred until the solid was completely dissolved to form a clear solution. The solution was slowly cooled down to room temperature and sealed stirred for about 2 days to form a precipitate. The precipitate was filtered, washed with methanol and then dried under vacuum at about 40° C. for about 7 h. The precipitate has an XRFD comprising peaks at about 25.47, 17.69, 27.23, 8.99, 6.68, 14.24, 20.27 and 19.67 degrees in term of two theta, wherein the XRFD substantially as depicted in FIG. 1.

Example 3

The compound of formula (I) (0.2 g) and ethanol (37.8 mL) were added to a reaction flask, heated to 80° C. and stirred until the solid was completely dissolved to form a clear solution. The solution was cooled down to room temperature and concentrated to about 5 mL under vacuum, then stirred at room temperature for about 1.5 h to form a precipitate. The precipitate was filtered, washed with ethanol and dried overnight under vacuum at about 30° C. to get a yellow solid. The solid was found to be crystalline form I through XRFD detecting.

Example 4

The compound of formula (I) (0.2 g) and methanol (22 mL) were added to a reaction flask, heated to 65° C. and stirred until the solid was completely dissolved to form a clear solution. The solution was cooled down to room temperature, stirred and evaporated naturally until 15 mL was left, and then sealed stirred at room temperature for about 6 h to form a precipitate. The precipitate was filtered, washed with methanol and dried overnight under vacuum at about 30° C. to get a solid. The solid was found to be crystalline form I through XRPD detecting.

Example 5

The compound of formula (I) (0.2 g) and acetone (48 mL) were added to a reaction flask, heated to 56° C. and stirred until the solid was completely dissolved to form a clear solution. The solution was cooled down to room temperature, stirred and evaporated naturally until 15 ml was left, and then sealed stirred at room temperature for about 2 days to form a precipitate. The precipitate was filtered and dried overnight under vacuum at about 40° C. to get a solid. The solid was found to be crystalline form I through XRPD detecting.

Example 6

The compound of formula (I) (0.2 g) and THF (18 mL) were added to a reaction flask, heated to 66° C. and stirred until the solid was completely dissolved to form a clear solution. The solution was cooled down to room temperature, stirred and evaporated naturally until 3 mL was left, and then sealed stirred at room temperature for about a day to form a precipitate. The precipitate was filtered and washed with THF, dried overnight under vacuum at about 30° C. to get a solid. The solid was found to be crystalline form I through XRPD detecting.

Example 7

The compound of formula (I) (0.2 g) and DCM (60 mL) were added to a reaction flask, heated to 44° C. and stirred until the solid was completely dissolved to form a clear solution. The solution was cooled down to room temperature, stirred and evaporated naturally until 20 mL was left, and then sealed stirred at room temperature for about 3 days to form a precipitate. The precipitate was filtered and washed with DCM, dried under vacuum at about 40° C. for about 7 h to get a solid. The solid was found to be crystalline form I through XRPD detecting.

Example 8

The compound of formula (I) (0.2 g) and 1, 4-dioxane (7 mL) were added to a reaction flask, heated to 101° C. and stirred until the solid was completely dissolved to form a clear solution. The solution was cooled down to room temperature, stirred and evaporated naturally until 5 mL was left, and then sealed stirred at room temperature for about 3 days to form a precipitate. The precipitate was filtered and washed with 1, 4-dioxane, dried under vacuum at about 40° C. for about 7 h to get a solid. The solid was found to be crystalline form I through XRPD detecting.

Example 9

The compound of Formula (I) (0.2 g) and ethylene glycol (15 mL) were added to a reaction flask, heated to 140° C. and stirred until the solid was completely dissolved to form a clear solution. The solution was cooled down to room temperature, stirred and evaporated naturally until 12 mL was left, and then sealed stirred at room temperature for about 3 days to form a precipitate. The precipitate was filtered and washed with ethylene glycol, dried under vacuum at about 40° C. for about 7 h to get a solid. The solid was found to be crystalline form I through XRPD detecting.

Example 10

The compound of formula (I) (0.2 g) and DMF (1 mL) were added to a reaction flask, heated to 70° C. and stirred until the solid was completely dissolved to form a clear solution, to the solution was added ethyl acetate, the resulting solution was slowly cooled down to room temperature and stirred for 2 h to form a precipitate. The precipitate was filtered and washed with ethyl acetate, dried overnight under vacuum at about 40° C. to get a solid. The solid was found to be crystalline form I through XRPD detecting.

Example 11

The compound of formula (I) (0.2 g) and ethylene DMF (1.0 mL) were added to a reaction flask, heated to 70° C. and stirred until the solid was completely dissolved to form a clear solution. 5 mL of water was then added dropwise to the solution. After that, the solution was slowly cooled down to room temperature and stirred for 2 h to form a precipitate. The precipitate was filtered and washed with some water, dried overnight under vacuum at about 40° C. to get a solid. The solid was found to be crystalline form I through XRPD detecting.

Example 12

The compound of formula (I) (0.2 g) and ethylene NMP (1.4 mL) were added to a reaction flask, heated to 70° C. and stirred until the solid was completely dissolved to form a clear solution. 5 mL of water was then added dropwise to the solution. After that, the mixture was slowly cooled down to room temperature and stirred for 3 h to form a precipitate. The precipitate was filtered and washed with some water, dried overnight under vacuum at about 40° C. to get a solid. The solid was found to be crystalline form I through XRPD detecting.

Example 13

The compound of formula (I) (0.2 g) and ethylene DMF (1 mL) were added to a reaction flask, heated to 70° C. and stirred until the solid was completely dissolved to form a clear solution. The 70° C. solution was added dropwise to EtOH (5 mL). After that, the mixture was slowly cooled down to room temperature and stirred for 2 h to form a precipitate. The precipitate was filtered and washed with EtOH, dried overnight under vacuum at about 40° C. to get a solid. The solid was found to be crystalline form I through XRPD detecting.

Example 14

The compound of formula (I) (1.0 g) and DMSO (3 mL) were added to a flask, heated to 80° C., after stirred for about 10 mins to the solution was added activated carbon (0.05 g) and stirred for another 30 min, then the temperature was reduced to below 50° C., filtered, the filtrate was heated to 80° C. and was added slowly to water (20 ml) with a temperature of 90° C., after adding, the temperature of the mixture was reduced to 25° C., after stirred for 2 hours, the precipitate was filtered and washed with water, dried under vacuum at about 70° C. for 12 h to get a solid. The water content of the solid is less than 1.0 wt %.

Example 15

The compound of formula (I) (0.2 g) and EtOH (4 mL) were added to a reaction flask, stirred at 50° C. for 5 days, filtered and washed with EtOH, dried overnight under vacuum at about 30° C. to get a solid. The solid was found to be crystalline form I through XRPD detecting.

Example 16-21

Preparation of Crystalline Form II of the Compound of Formula (I)

Example 16

Figure 3:
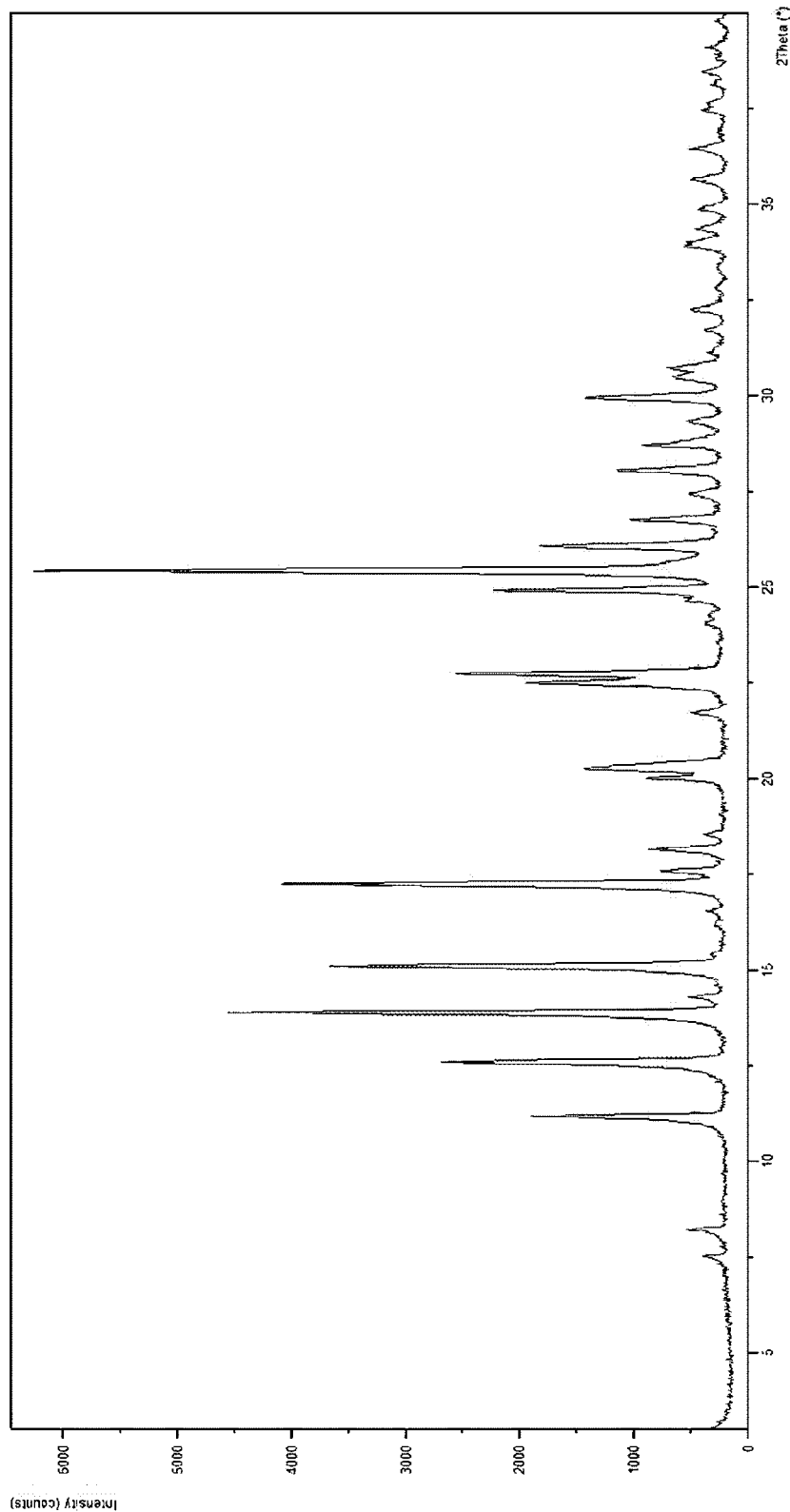
FIG. 3 depicts the X-ray powder diffractogram of the crystalline form II of the compound of formula (I) according to one example of present disclosure.
Figure 4:
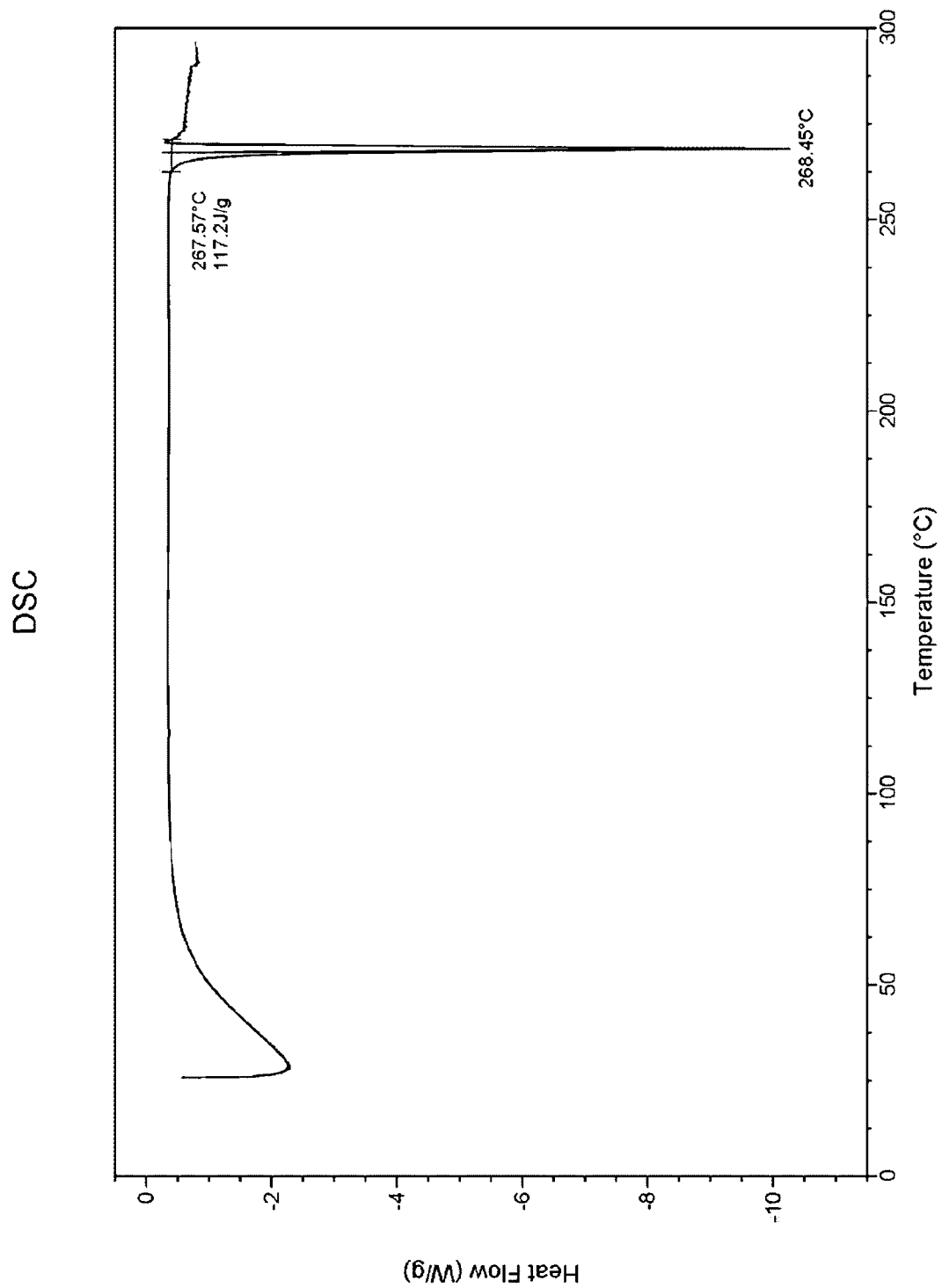
FIG. 4 depicts the differential scanning calorimeter (DSC) curve of the crystalline form II of the compound of formula (I) according to one example of present disclosure.

The compound of formula (I) (0.2 g) and ethanol (30 mL) were added to a reaction flask, heated to reflux and stirred until the solid was completely dissolved to form a clear solution. The solution was slowly cooled down to room temperature and sealed stirred for about 2 days to form a precipitate. The precipitate was filtered, washed with ethanol and then dried under vacuum at about 40° C. for about 7 h. The precipitate has an XRFD comprising peaks at about 25.40, 13.86, 17.21 and 22.71 degrees in term of two theta, wherein the XRFD substantially as depicted in FIG. 3.

Example 17

The compound of formula (I) (0.2 g) and isopropanol (49 mL) were added to a reaction flask, heated to reflux and stirred until the solid was completely dissolved to form a clear solution. The solution was slowly cooled down to room temperature and sealed stirred for about a day to form a precipitate. The precipitate was filtered, washed with isopropanol and then dried under vacuum at about 40° C. for about 7 h to get a solid. The solid was found to be crystalline form II through XRFD detecting.

Example 18

The compound of formula (I) (0.2 g) and n-butanol (10 mL) were added to a reaction flask, heated to reflux and stirred until the solid was completely dissolved to form a clear solution. The solution was slowly cooled down to room temperature and sealed stirred for about a day to form a precipitate. The precipitate was filtered, washed with n-butanol and then dried under vacuum at about 40° C. for about 7 h to get a solid. The solid was found to be crystalline form II through XRFD detecting.

Example 19

The compound of formula (I) (0.2 g) and ethylene glycol (5 mL) were added to a reaction flask, heated to about 140° C. and stirred until the solid was completely dissolved to form a clear solution. The solution was slowly cooled down to room temperature and sealed stirred for about a day to form a precipitate. The precipitate was filtered, washed with ethylene glycol and then dried under vacuum at about 40° C. for about 7 h to get a solid. The solid was found to be crystalline form II through XRFD detecting.

Example 20

The compound of formula (I) (0.2 g) and tert-butanol (78 mL) were added to a reaction flask, heated to reflux and stirred until the solid was completely dissolved to form a clear solution. The solution was slowly cooled down to room temperature and sealed stirred for about 2 days to form a precipitate. The precipitate was filtered, washed with tert-butanol and then dried under vacuum at about 40° C. for about 7 h to get a solid. The solid was found to be crystalline form II through XRFD detecting.

Example 21

The compound of formula (I) (0.2 g) and DMSO (1 mL) were added to a reaction flask, stirred at room temperature until the solid was completely dissolved to form a clear solution. The solution was added dropwise to water (5 mL). After that, the mixture was continuously stirred for 2 h, filtrated and washed with water, dried overnight under vacuum at about 40° C. to get a solid. The solid was found to be crystalline form II through XRPD detecting.

Example 22-29

Preparation of Crystalline Form III of the Compound of Formula (I)

Example 22

Figure 5:
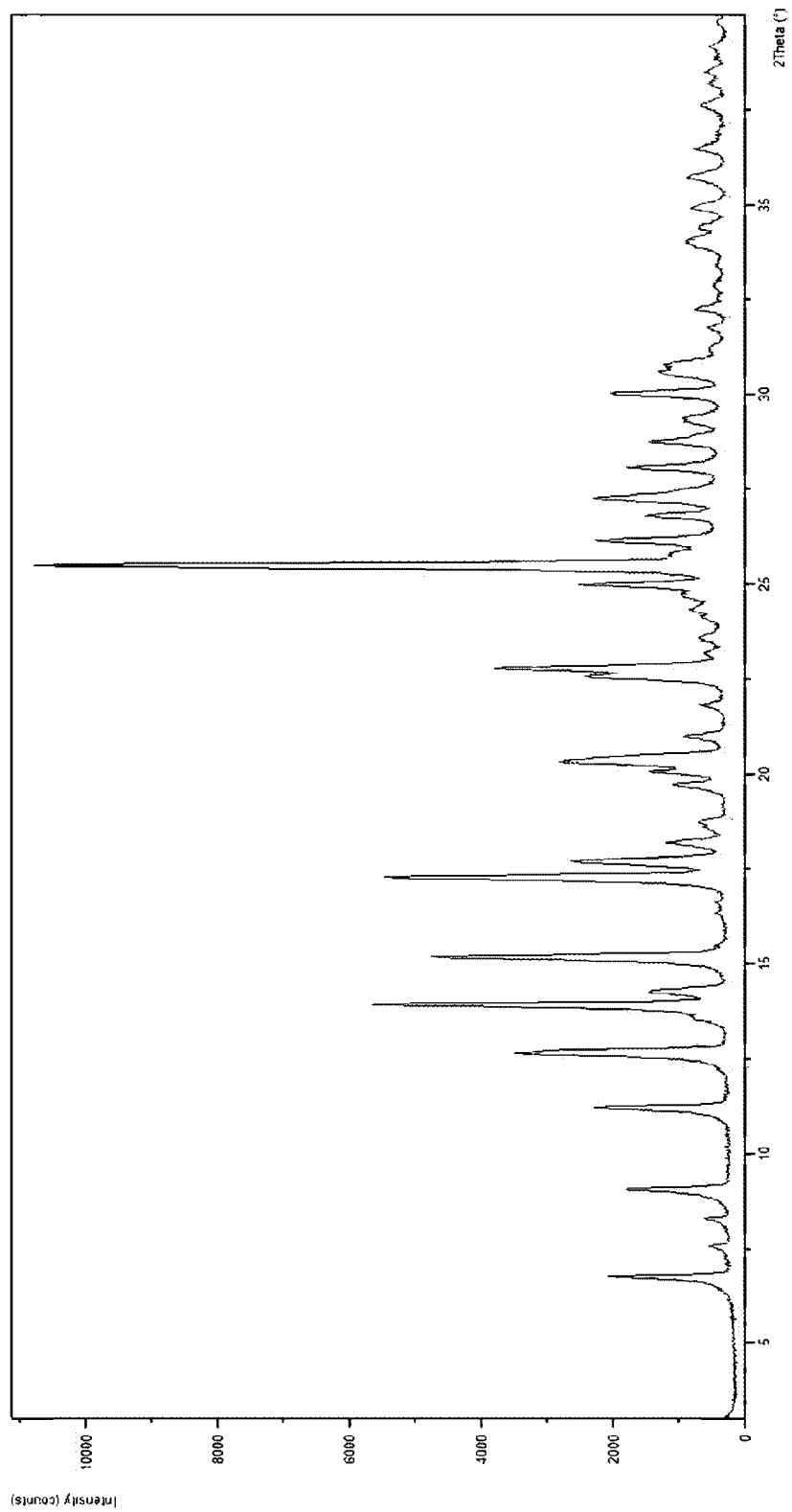
FIG. 5 depicts the X-ray powder diffractogram of the crystalline form III of the compound of formula (I) according to one example of present disclosure.
Figure 6:
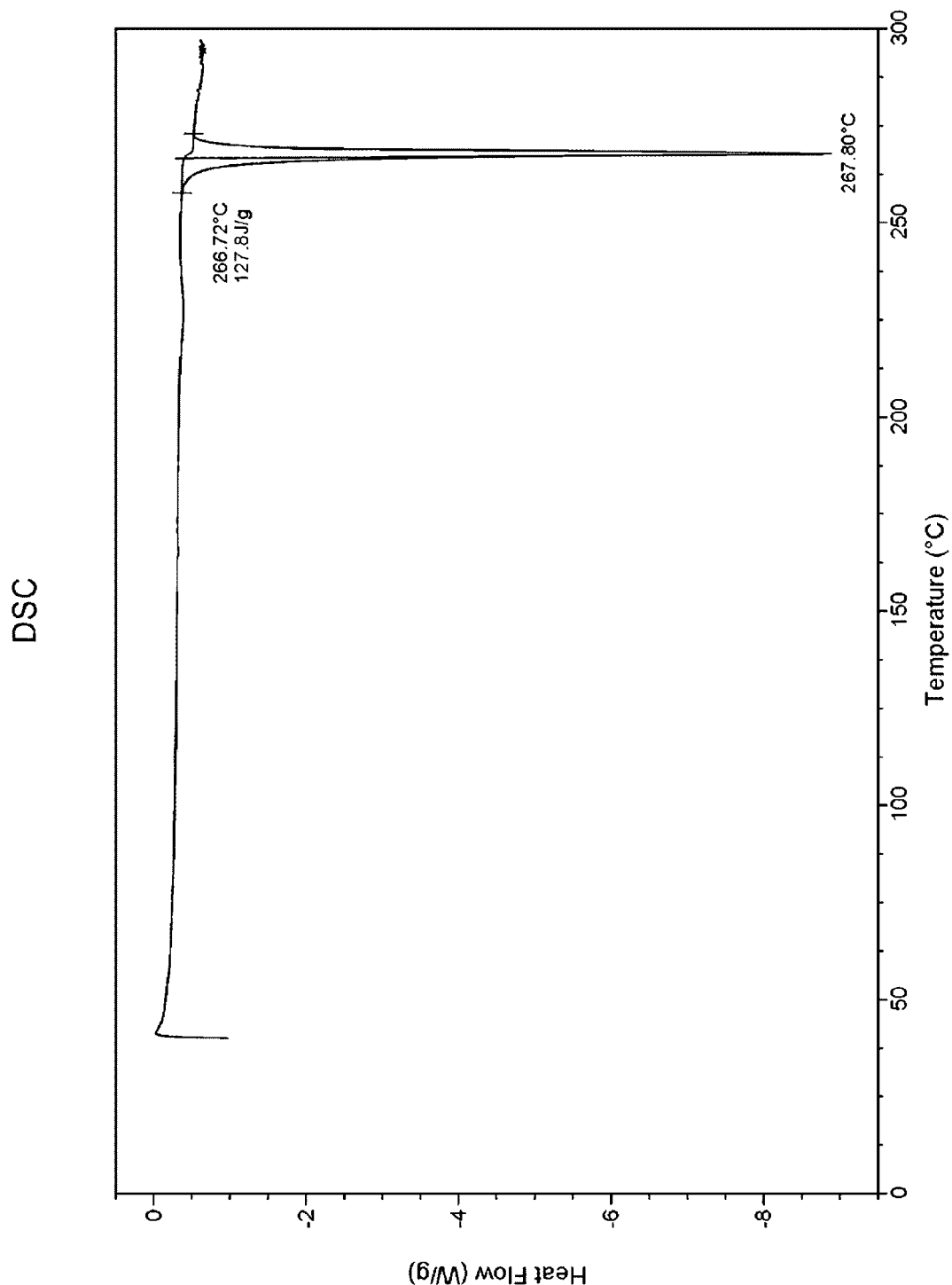
FIG. 6 depicts the differential scanning calorimeter (DSC) curve of the crystalline form III of the compound of formula (I) according to one example of present disclosure.

The compound of formula (I) (0.2 g) and n-propanol (17 mL) were added to a reaction flask, heated to reflux and stirred until the solid was completely dissolved to form a clear solution. The solution was slowly cooled down to room temperature and sealed stirred for about 2 days to form a precipitate. The precipitate was filtered, washed with n-propanol and then dried under vacuum at about 40° C. for about 7 h. The precipitate has an XRPD comprising peaks at about 25.44, 13.88 and 17.23 degrees in term of two theta, wherein the XRPD substantially as depicted in FIG. 5.

Example 23

The compound of formula (I) (0.2 g) and 1, 4-dioxane (5 mL) were added to a reaction flask, heated to reflux and stirred until the solid was completely dissolved to form a clear solution. The solution was slowly cooled down to room temperature and sealed stirred for about 4 days to form a precipitate. The precipitate was filtered, washed with 1,4-dioxane and then dried under vacuum at about 40° C. for about 15 h to get a solid. The solid was found to be crystalline form III through XRPD detecting.

Example 24

The compound of formula (I) (0.2 g) and acetonitrile (24 mL) were added to a reaction flask, heated to reflux and stirred until the solid was completely dissolved to form a clear solution. The solution was slowly cooled down to room temperature and sealed stirred for about 2 days to form a precipitate. The precipitate was filtered, washed with acetonitril and then dried under vacuum at about 40° C. for about 15 h to get a solid. The solid was found to be crystalline form III through XRPD detecting.

Example 25

The compound of formula (I) (0.2 g) and isopropyl acetate (195 mL) were added to a reaction flask, heated to reflux and stirred until the solid was completely dissolved to form a clear solution. The solution was slowly cooled down to room temperature and sealed stirred for about 3 days to form a precipitate. The precipitate was filtered, washed with isopropyl acetate and then dried under vacuum at about 40° C. for about 15 h to get a solid. The solid was found to be crystalline form III through XRPD detecting.

Example 26

The compound of formula (I) (0.2 g) and NMP (1.4 mL) were added to a reaction flask, heated to about 70° C. and stirred until the solid was completely dissolved to form a clear solution. The solution was slowly cooled down to room temperature and added dropwise to water (5 mL). After that, the mixture was continuously stirred for 2 h, filtrated and washed with water, dried overnight under vacuum at about 40° C. to get a solid. The solid was found to be crystalline form III through XRPD detecting.

Example 27

The compound of formula (I) (0.2 g) and DMSO (1 mL) were added to a reaction flask, stirred at room temperature until the solid was completely dissolved to form a clear solution. The solution was added dropwise to EtOH (5 mL) to form a mixture, after being stirred for 0.5 h, the mixture was added dropwise to water (10 mL) and continuously stirred for 5 h and then filtrated and washed with water, dried overnight under vacuum at about 40° C. to get a solid. The solid was found to be crystalline form III through XRPD detecting.

Example 28

The compound of formula (I) (0.2 g) and DMSO (1 mL) were added to a reaction flask, stirred at room temperature until the solid was completely dissolved to form a clear solution. Water (5 mL) was added dropwise to the solution. Then, continuously stirred for 3 h, filtrated and washed with water, dried overnight under vacuum at about 40° C. to get a solid. The solid was found to be crystalline form III through XRPD detecting.

Example 29

The compound of formula (I) (0.2 g) and DMF (1 mL) were added to a reaction flask, heated to about 70° C. and stirred until the solid was completely dissolved to form a clear solution. The solution was slowly cooled down to room temperature and added dropwise to water (5 mL). After that, the mixture was continuously stirred for 2 h, filtrated and washed with water, dried overnight under vacuum at about 40° C. to get a solid. The solid was found to be crystalline form III through XRPD detecting.

Example 30

Preparation of Crystalline Form IV of the Compound of Formula (I)

Figure 7:
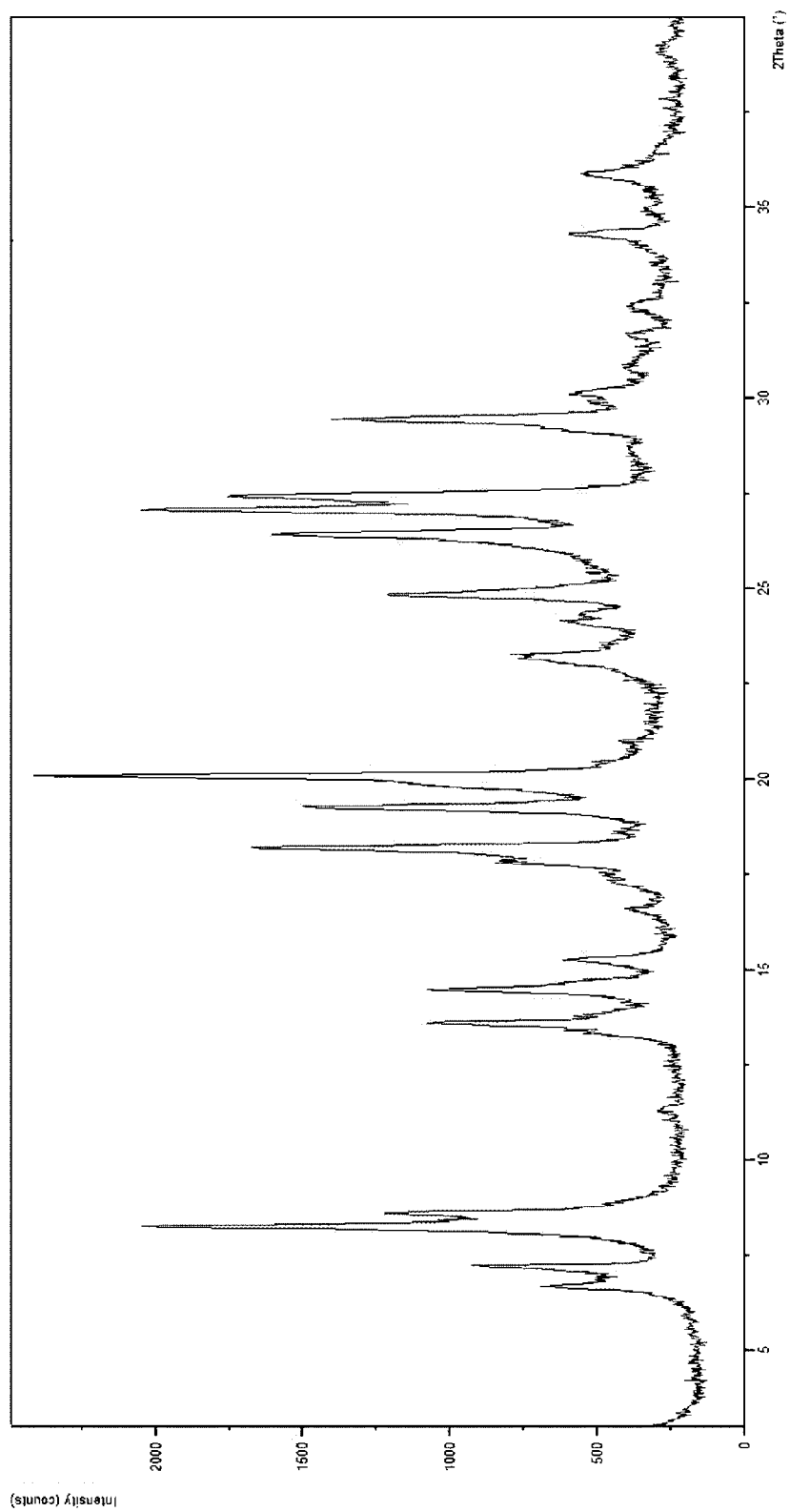
FIG. 7 depicts the X-ray powder diffractogram of the crystalline form IV of the compound of formula (I) according to one example of present disclosure.
Figure 8:
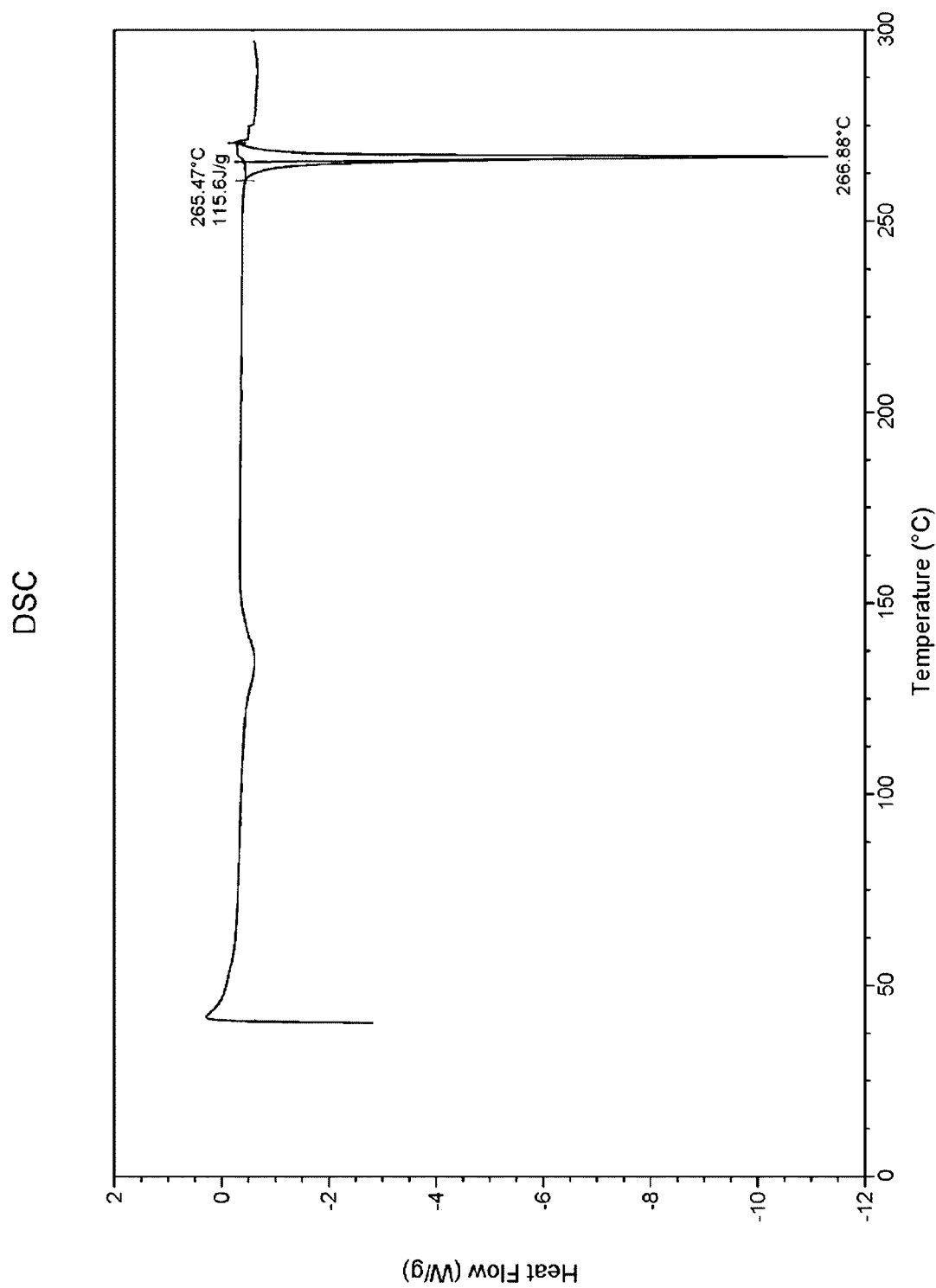
FIG. 8 depicts the differential scanning calorimeter (DSC) curve of the crystalline form IV of the compound of formula (I) according to one example of present disclosure.

The compound of formula (I) (0.2 g) and n-butanone (39 mL) were added to a reaction flask, heated to reflux and stirred until the solid was completely dissolved to form a clear solution. The solution was slowly cooled down to room temperature and sealed stirred for about 3 days to form a precipitate. The precipitate was filtered, washed with n-butanone and then dried under vacuum at about 40° C. for about 15 h. The precipitate has an XRPD comprising peaks at about 20.01, 27.03, 8.21 degrees in term of two theta, wherein the XRPD substantially as depicted in FIG. 7.

Example 31

The Instrument Parameters Settings and the Detecting Method Thereof

1. X-Ray Powder Diffractogram:
Using Cu tagret/Kα/1.54 Å radiation in the power of 45 kV/40 mA of PANalytical EmpyreanX-ray diffractometer to collect the data from 3°~40° in term of two theta. The step size is 0.0168° and the scanning rate is 10 s/step. Continuously rotate sample to reduce the impact of preferred orientations.

2. Differential Scanning Calorimeter (DSC) Curve

Collect the thermographs from equipment of TA Q2000. The samples are weighed in T-zero aluminous sample plate, gland, the temperature rise from 40° C. to 300° C. in the rising speed of 10° C./min, the sample is analyzed in nitrogen atmosphere.

Example 32

Stability Test of Crystalline Form I, III of the Compound of Formula (I)

1 Sample Package and Storage

The sample was tied with double low density polyethylene film and was placed in the following conditions: 40° C.±2° C./75% RH±5% for 30 days. The purity of the sample was determined by HPLC at the first day and the thirtieth day.

3 the Acceleration Test Result was Showed in Table 1:

TABLE 1

The acceleration test result of the crystalline form I

| No. | number of days | appearance | impurity A (%) | impurity B (%) | purity (%) | Overall impurity (%) | XRD | DSC |
|---|---|---|---|---|---|---|---|---|
| 1 | 0 | Off-white powder | 0.06 | 0.26 | 99.6 | 0.44 | Shows characteristic peaks of form I | Shows characteristic peaks of form I |
|  | 30 | Off-white powder | 0.06 | 0.26 | 99.6 | 0.43 | Yes | Yes |

TABLE 2

The acceleration test result of crystalline form III

| No. | days | appearance | impurity A (%) | impurity B (%) | purity (%) | Overall impurity (%) | XRD | DSC |
|---|---|---|---|---|---|---|---|---|
| 1 | 0 | pale yellow powder | 0.05 | 0.35 | 99.4 | 0.65 | Show characteristic peaks of crystalline III | Show characteristic peaks of crystalline III |
|  | 30 | pale yellow powder | 0.04 | 0.34 | 99.4 | 0.57 | Yes | Yes |

Conclusion: as show in table 2, the appearance and the related substance of crystalline form I and form III of compound of formula (I) did not change in the conditions of 40° C.±2° C./75% RH±5%, and the crystalline form did not change neither. Indicate that crystalline form I and form III can be stable for a month in the conditions of 40° C.±2° C./75% RH±5%.

2 Chromatographic Condition
Chromatographic Column: Agilent RX C8, 4.6×250 mm, 5 μm;
Detector: UV detector, wavelength: 260 nm;
flow rate: 1.0 ml/min;
column temperature: 40° C.;
input dosage: 10 μL;
running time: 59 min;
Preparation the buffer solution: Sodium 1-octanesulfonate 2.0 g was dissolved in 1000 ml of water, then was added 2 mL of phosphoric acid, The resulted solution was stirred and filtered. The mobile phase includes phase A and phase B, wherein phase A is a mixture of buffer solution and acetonitrile=90:10; with a ratio 90/10 (V/V), Phase B is acetonitrile; Table 3 shows the gradient elution program of mobile phase:

| Time (min) | Phase A (%) | Phase B (%) |
|---|---|---|
| 0 | 73 | 27 |
| 20 | 73 | 27 |
| 51 | 51 | 65 |
| 52 | 73 | 27 |
| 59 | 73 | 27 |

Example 33

Hygroscopicity Test of Crystalline Form I and Form III of the Compound of Formula (I)

1 Instrument and Regents
1.1 Instrument: 1/100000 Scale, XP205DR 1.2 Test Method According to "Chinese Pharmacopoeia"2010 edition, proportion II, XI X J.

1) Keep a dry glass weighing bottle with stopper (external diameter: 50 mm, height: 15 mm) in 25° C.±1° C. of thermostatic drier with saturated solution of ammonium chloride or ammonium sulfate placing on the bottom, precisely weighed (m1).

2) An appropriate amount of sample was spread in the weighing bottle by a millimeter thick, precisely weighed (m2).

3) An open weighing bottle and lid were kept together in environment of constant temperature and humidity for about 24 h.

4) Lid the weighing bottle and precisely weighed (m3).

weight gain ratio=$(m3-m2)/(m2-m1)\times 100\%$

5) Table 4 shows the result judgement of hygroscopicity

| NO. | Hygroscopic properties | Weight gain by sorption |
|---|---|---|
| 1 | hygroscopy | Absorb sufficient moisture to form liquid |
| 2 | Strong hygroscopic | ≥15% |
| 3 | hygroscopic | ≥2%, <15% |
| 4 | slightly hygroscopic | ≥0.2%, <2% |
| 5 | Low hygroscopic | <0.2% |

5) Experiment results

TABLE 5

Hygroscopicity results of crystalline form I of the compound of formula (I)

| # | m1 (g) | m2 (g) | m3 (g) | Weight gain by absorption (%) | Result |
|---|---|---|---|---|---|
| 1 | 28.50004 | 29.00050 | 29.00098 | 0.1% | Low hygroscopic |

TABLE 6

Hygroscopicity results of crystalline form III of the compound of formula (I)

| # | m1 (g) | m2 (g) | m3 (g) | Weight gain by absorption (%) | Result |
|---|---|---|---|---|---|
| 1 | 31.58213 | 31.97061 | 31.97077 | 0.04% | Low hygroscopic |

Those illustrative embodiments herein are used to help understand the method and core ideas about this present invention. In should be noted that many adaptation and modifications may be made without departing from the scope of the appended claims in accordance with the common general knowledge of those of ordinary skilled in the art.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A crystalline form of compound of formula (I), wherein the crystalline form is form III or form IV

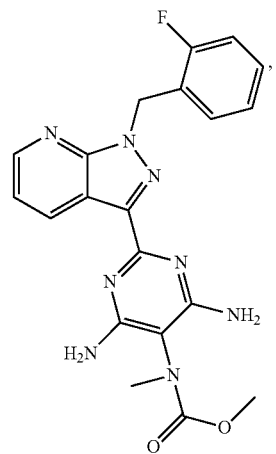

(I)

wherein form III has an X-ray powder diffraction pattern comprising peaks at 6.68±0.2, 9.02±0.2, 25.44±0.2, 13.88±0.2, 17.23±0.2, 15.14±0.2 degrees in term of two theta; and wherein the peak at 25.44±0.2 degree is the strongest peak in the XRPD of form III, and wherein form IV has an X-ray powder diffraction pattern comprising peaks at 20.01±0.2, 27.03±0.2, 8.21±0.2, 18.15±0.2 and 27.38±0.2 degrees in term of two theta, and wherein the peak at 20.01±0.2 degree is the strongest peak in the XRPD of form IV.

2. The crystalline form of claim 1, wherein the crystalline form is form III comprising peaks at 25.44±0.2, 13.88±0.2, 17.23±0.2, 15.14±0.2, 22.75±0.2, 12.60±0.2, 11.17±0.2, 9.02±0.2, 17.66±0.2, 22.52±0.2, 24.94±0.2, 17.53±0.2 and 6.68±0.2 degrees in term of two theta.

3. The crystalline form of claim 1, wherein the crystalline form is form IV comprising peaks at 20.01±0.2, 27.03±0.2, 8.21±0.2, 18.15±0.2, 27.38±0.2, 19.22±0.2, 26.34±0.2, 29.38±0.2, 8.57±0.2, 14.45±0.2 and 7.15±0.2 degrees in term of two theta.

4. A process for preparing the crystalline form of claim 1, comprising: dissolving any solid forms of the compound of formula (I) in a good solvent to form a solution; forming crystals by reducing the temperature of the solution or removing proportion of the solvent or adding an anti-solvent to the solution; and collecting the crystal.

5. The process of claim 4, wherein the temperature of the solution is reduced to from about −10° C. to about 40° C.

6. The process of claim 4, wherein the crystal is formed at room temperature.

7. The process of claim 4, wherein the method of removing proportion of the solvent comprising distillation or evaporation or any combine thereof.

8. The process of any one claim 4, wherein the amount of the removed solvent is about 20% to about 90% with respect to the total volume of the solution.

9. The process of any one claim 4, wherein the amount of the removed solvent is about 30% with respect to the total volume of the solution.

10. A process for preparing the crystalline form of claim 1, comprising dissolving the compound of formula (I) in a good solvent at room temperature to form a solution, and forming crystals by adding the solution to an anti-solvent or adding an anti-solvent to the solution.

11. The process of claim 4, wherein the good solvent or anti-solvent is selected from one or more of NMP, DMF, water, methanol, ethanol, ethylene glycol, isopropanol, n-propanol, n-butanol, tert-butanol, THF, methylene chloride, DMSO, ethyl acetate, isopropyl acetate, butanone, acetone, acetonitrile and 1,4-dioxane.

12. The process of claim 11, wherein the process for preparing the crystalline form III of the compound of formula (I), comprises:

mixing the compound of formula (I) with 1,4-dioxane, heating the resulting mixture to reflux and stirring the mixture until the solid is completely dissolved to form a solution, slowly cooling the solution to room temperature, and stirring the solution for about 1 h to 300 h and collecting the crystals.

13. The process of claim 11, wherein the crystalline form IV of the compound of formula (I) is formed, and wherein the good solvent is butanone.

14. A pharmaceutical composition comprising a therapeutically effective amount of the crystalline form of claim 1 and one or more pharmaceutically acceptable carriers or excipients.

15. The process of claim 10, wherein the good solvent or anti-solvent is selected from one or more of NMP, DMF, water, methanol, ethanol, ethylene glycol, isopropanol, n-propanol, n-butanol, tert-butanol, THF, methylene chloride, DMSO, ethyl acetate, isopropyl acetate, butanone, acetone, acetonitrile and 1,4-dioxane.

16. A method of treating cardiovascular diseases, thromboembolic diseases, ischemia, hypertension or treating sexual dysfunction in a patient by administering to the patient with the crystalline form of claim 1.

17. A method of treating cardiovascular diseases, thromboembolic diseases, ischemia, hypertension or treating sexual dysfunction in a patient by administering to the patient with the pharmaceutical composition of claim 14.

* * * * *